United States Patent [19]

Jacquet et al.

[11] 4,348,380

[45] Sep. 7, 1982

[54] COSMETIC COMPOSITIONS FOR THE HAIR AND SKIN BASED ON COPOLYMERS HAVING TERTIARY AMINE AND/OR QUATERNARY AMMONIUM FUNCTIONS

[75] Inventors: Bernard Jacquet, Antony; Christos Papantoniou, Montmorency; Jean Mondet, Sevran, all of France

[73] Assignee: L'Oreal, Paris, France

[21] Appl. No.: 66,678

[22] Filed: Aug. 14, 1979

[30] Foreign Application Priority Data

May 17, 1977 [FR] France .............................. 77 15088

[51] Int. Cl.$^3$ .......................... A61K 7/00; A61K 7/06; A61K 31/74; C11D 3/48
[52] U.S. Cl. .......................................... 424/47; 8/405; 8/406; 424/59; 424/60; 424/63; 424/65; 424/70; 424/78; 424/80; 424/81; 424/168; 252/106
[58] Field of Search .................................... 424/47, 70

[56] References Cited

U.S. PATENT DOCUMENTS

| | | | |
|---|---|---|---|
| 3,306,875 | 2/1967 | Hay | 260/47 |
| 3,862,091 | 1/1975 | Barabas | 260/73 L |
| 3,912,808 | 10/1975 | Sokol | 424/71 |
| 3,966,087 | 6/1976 | Curry et al. | 424/47 |
| 3,986,825 | 10/1976 | Sokol | 424/70 |
| 4,009,255 | 2/1977 | Kalopessis et al. | 424/70 |

*Primary Examiner*—Dale R. Ore
*Attorney, Agent, or Firm*—Cushman, Darby & Cushman

[57] ABSTRACT

A cosmetic composition for the care of the hair and the skin comprises a cosmetic vehicle and at least one copolymer having one or both of tertiary amine and quaternary ammonium functions. The copolymer, which can have a molecular weight between 2,000 and 500,000 is present in the composition in an amount between 0.01 and 15 percent by weight thereof.

7 Claims, No Drawings

COSMETIC COMPOSITIONS FOR THE HAIR AND SKIN BASED ON COPOLYMERS HAVING TERTIARY AMINE AND/OR QUATERNARY AMMONIUM FUNCTIONS

The present invention relates to new cosmetic compositions based on copolymers having tertiary amine and/or quaternary ammonium functions and to their use for the care of the hair and the skin.

For a certain number of years now, it has been proposed to use for the care of the hair and the skin, certain copolymers having tertiary amine and/or quaternary ammonium functions.

In effect, it was noted that these copolymers had a certain affinity for the keratin of the hair and the skin, and their use consequently avoided a certain sensation of dryness and roughness of the hair and skin.

However, it was established that these copolymers exhibited a certain incompatibility with some cosmetic compositions so that consequently their use has been considerably limited.

Moreover, it was established that the affinity of these copolymers for the hair or skin was not sufficiently long lasting. Consequently, it was necessary to repeat their application quite frequently so as to give to the skin and to the hair a natural appearance, an agreeable appearance and an agreeable touch or feel.

It has now been discovered, in a surprising way, that by using a new class of copolymers having tertiary amine and/or quaternary ammonium functions it is possible on the one hand to obtain a large variety of cosmetic formulations without encountering the difficulties noted with previously known copolymers, and on the other hand to obtain a long lasting effect, taking into account the greater affinity of the copolymers used in accordance with the invention vis-a-vis the keratin of the hair and the skin.

The present invention thus relates to a new cosmetic composition for the care of the hair and the skin containing in an appropriate cosmetic vehicle at least one copolymer having tertiary amine and/or quaternary ammonium functions, the said copolymer having the formula:

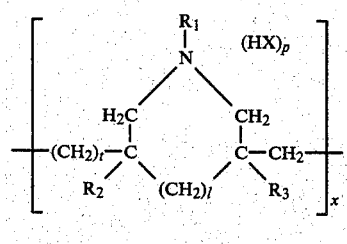

Ia

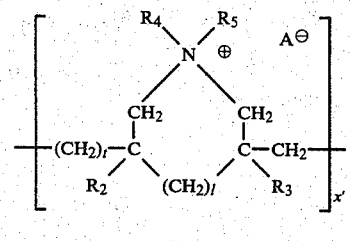

Ib

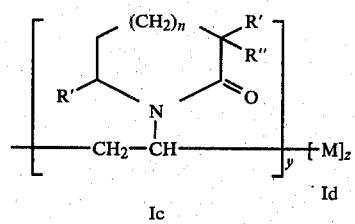

Ic

Id wherein
$R_1$, $R_4$ and $R_5$, each independently represent alkyl having 1-12 carbon atoms,
$R_2$ and $R_3$ each independently represent hydrogen or methyl,
$R'$ and $R''$ each independently represent hydrogen or lower alkyl having 1-4 carbon atoms,
l is 0 or 1, if l is 0, t=1, and if l is 1, t=0,
n is 0, 1 or 2,
p is 0 or 1,
A represents an anion, and preferably a chloride or bromide anion,
HX is a mineral or organic acid, and preferably an acid selected from the group consisting of hydrochloric acid, hydrobromic acid, acetic acid and lactic acid,
M represents a unit of a polymerizable unsaturated monomer,
$x+x'$ corresponds to 95-5 mole percent, x or x' being able to be 0,
y corresponds to 5-95 mole percent, and
z corresponds to 0-60 mole percent, $(x+x')+y+z$ being equal to 100 mole percent.

Representative unsaturated monomers providing the units of formula M (Id) include particularly:
(i) vinyl esters of the formula:

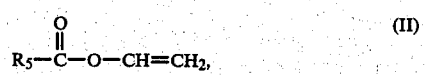

(II)

wherein $R_5$ represents alkyl having 1-17 carbon atoms,
(ii) vinyl ethers of the formula

(III), wherein $R_6$ represents alkyl having 1-16 carbon atoms,
(iii) acrylic or methacrylic esters of the formula

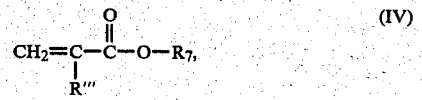

(IV)

wherein
$R'''$ represents hydrogen or methyl, and
$R_7$ represents a member selected from the group consisting of alkyl, linear or branched, having 1-18 carbon atoms, alkyl having 1-3 carbon atoms and substituted by at least one alkoxy having 1-4 carbon atoms, and a radical of the formula

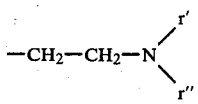

wherein r' and r" each independently represent alkyl having 1-4 carbon atoms, (iv) acrylamides or methacrylamides of the formula

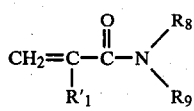

wherein $R_8$ and $R_9$ each independently represent hydrogen, linear or branched alkyl having 1-4 carbon atoms or $-(CH_2)_m-OH$ wherein m is equal to 1, 2 or 3, and $R'_1$ represents hydrogen or methyl.

In accordance with a first preferred embodiment of the present invention, the copolymers have the formula:

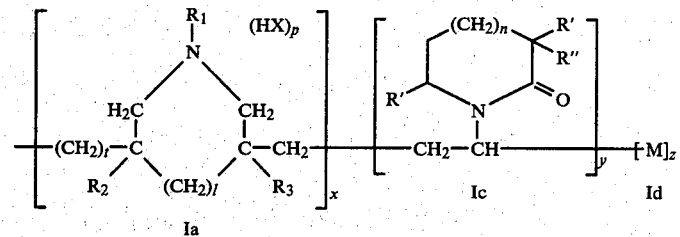

wherein $R_1$, $R_2$, $R_3$, R', R", M, HX, l, t, p and n have the same meanings given above, x corresponds to 95-5 mole percent,
y corresponds to 5-95 mole percent and
z corresponds to 0-60 mole percent.

In accordance with a second preferred embodiment of the invention, the copolymers have the formula:

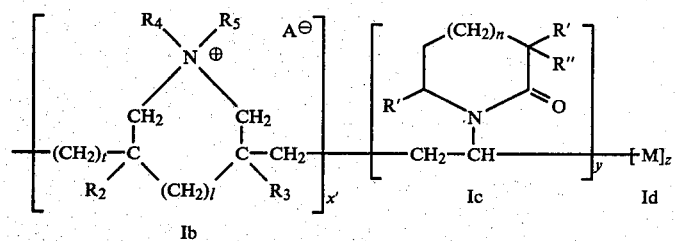

wherein $R_2$, $R_3$, $R_4$, $R_5$, R', R", M, A, l, t and n have the same meanings given above, x' corresponds to 95-5 mole percent,
y corresponds to 5-95 mole percent and
z corresponds to 0-60 mole percent.

In accordance with a third preferred embodiment of the invention, the copolymers can have both units Ia and Ib in addition to units Ic and optionally units Id.

The copolymers useful in the present invention exhibit the characteristics of being both soluble in water and in alcohols, principally ethanol and isopropanol.

The copolymers have a molecular weight between 2,000 and 500,000 and preferably between 4,000 and 75,000.

Units Ia of the copolymers are obtained by cyclopolymerization of a salified diallyl alkyl amine, having the formula:

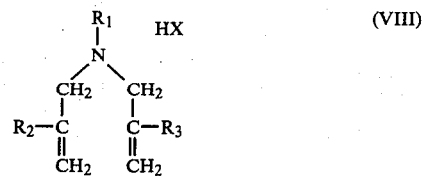

(VIII)

wherein $R_1$, $R_2$, $R_3$ and HX have the same meanings given above, and the units (Ib) of the copolymers are obtained by cyclopolymerization of a quaternary ammonium salt, and principally of a diallyl dialkyl ammonium chloride or bromide having the formula (IX)

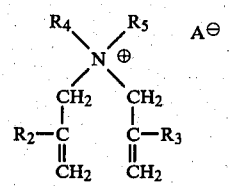

wherein $R_2$, $R_3$, $R_4$, $R_5$ and A have the same meanings given above.

In effect, during the polymerization of the diallyl compounds of formulas (VIII) and (IX) with an N-vinyl lactam, either alone or in admixture with another monomer, they cyclize to produce units (Ia) and (Ib) respectively having either five or six elements in the cyclic structure.

Representative salified diallyl alkyl amines of formula (VIII) include in particular: the hydrochlorides, hydrobromides, acetates and lactates of methyl diallylamine, ethyl diallylamine, butyl diallylamine, octyl diallylamine, decyl diallylamine and dodecyl diallylamine.

Representative diallyl dialkyl ammonium chlorides and bromides of formula (IX) include: the chlorides or bromides of dimethyl diallyl ammonium, methyl ethyl diallyl ammonium, methyl butyl diallyl ammonium and methyl dodecyl diallyl ammonium.

Representative N-vinyl lactams providing the units of formula (Ic) include: N-vinylpyrrolidone-2, N-vinyl-piperidone-2, N-vinyl caprolactam, N-vinyl methyl-5-pyrrolidone-2 and N-vinyl dimethyl-3,3-pyrrolidone-2.

According to a preferred embodiment of the invention, N-vinylpyrrolidone-2 is employed.

Representative unsaturated monomers providing units M, (Id) which are capable of being polymerized with the diallyl monomer and the N-vinyl lactam include, in particular:

(i) as the vinyl esters of formula (II): vinyl acetate, vinyl propionate, vinyl butyrate, vinyl laurate and vinyl stearate;

(ii) as the vinyl ethers of formula (III): methyl vinyl ether, ethyl vinyl ether, isopropyl vinyl ether, ethyl hexyl vinyl ether, dodecyl vinyl ether and hexadecyl vinyl ether;

(iii) as the acrylates and methacrylates of formula (IV): the acrylates and methacrylates of methyl, ethyl, propyl, isopropyl, butyl, isobutyl, s-butyl, (2-methyl)butyl, (3-methyl)butyl, (2-ethyl)butyl, amyl, (3-methyl)hexyl, (3-ethyl)hexyl, (2-ethyl)-hexyl, (2-methoxy)ethyl and (2-ethoxy)ethyl, as well as the acrylates and methacrylates of N,N-dimethylamino-2 ethyl and N,N-diethylamino-2 ethyl, optionally quaternized with the aid of dimethyl sulfate, ethyl bromide or any other quaternization agent, and (iv) as the acrylamides and methacrylamides of formula (V): acrylamide, methacrylamide, N-methylacrylamide, N-tert-butylacrylamide, N-hydroxymethyl acrylamide, N-(1,1-dimethyl-2-hydroxy) 1-ethyl acrylamide and the N,N-dimethyl, N,N-diethyl, N,N-dibutyl, and N,N-diisobutyl acrylamides and methacrylamides.

Certain ones of the copolymers used in the composition of the invention are known and their preparation is described in U.S. Pat. No. 3,862,091.

The other copolymers are obtained in accordance with the same operating procedures by copolymerization in emulsion or in solution in water or an organic liquid such as for example ethanol, methanol, benzene, toluene, xylene or other solvents.

The polymerization catalysts are of a conventional type, such as for example, hydrogen peroxide, benzoyl peroxide, azo-bis-isobutyronitrile, but preferably t-butylperoxypivalate or t-butyl hydroperoxide is employed.

The polymerization reaction can also be initiated by irradiation or by oxidation-reduction systems such as a hydrogen peroxide/ferrous chloride couple or an ammonium persulfate/ferrous chloride couple.

The polymerization is generally carried out at a temperature between 30° and 150° C. and preferably between 60° and 90° C.

When it is desired to obtain polymers of formula (VI) in which the Ia units are provided in the form of free amines, the polymers obtained in salified form are submitted to a treatment with a base such as, for example, sodium hydroxide at ambient temperature.

The cosmetic compositions in accordance with the present invention containing the copolymers such as they are defined above can be provided under different forms.

The cosmetic compositions according to the invention can contain copolymers of formula (I) either as the principal active component or as an additive.

Moreover, these compositions generally contain at least one conventional adjuvant used in cosmetic compositions.

The cosmetic compositions can be provided in the form of aqueous, alcoholic or hydroalcoholic solutions, the alcohol being principally a lower alkanol such as ethanol or isopropanol, or in the form of a cream, a gel, an emulsion or even in the form of an aerosol packaged under pressure in an aerosol container together with a propellant.

The adjuvants generally provided in the cosmetic compositions according to the invention are, for example, perfumes, dyes, preservatives, sequesterants, thickening agents and the like.

It is appropriate to remark that the cosmetic compositions according to the invention are either compositions ready for use or concentrates which can be diluted before use.

The cosmetic compositions according to the invention then are not limited to a particular concentration of the copolymer of formula (I).

Generally, in the cosmetic compositions according to the invention, the concentration of the copolymer of formula I is between 0.01 and 15 weight percent and preferably between 0.1 and 10 weight percent.

As has been indicated above, the copolymers of formula (I) exhibit principally interesting cosmetic characteristics when they are applied to the hair.

Thus when they are applied to living human hair either alone, or with other active substances during a hair treatment such as a shampooing, a hair dyeing, a hair setting or the like, they improve significantly the qualities of the hair and impart thereto, principally, suppleness and a beautiful luster.

Moreover, they assist the particular hair treatment and facilitate the combing of wet hair. Contrary to previously known copolymers they do not render dry hair heavy and they facilitate the achievement of bouffant type hair styles. Moreover, they contribute effectively to the elimination of defects of hair sensitized by chemical treatments or by degradation caused by atmospheric air, the sun or sea water.

The copolymers used in the cosmetic compositions of the invention are particularly interesting when they are used as pre-treating agents, principally with an anionic and/or nonionic shampoo or before an oxidation hair dyeing, itself followed by an anionic and/or nonionic shampoo.

The hair, thus treated, is particularly easy to comb and has a very soft touch.

They are also useful as pre-treating agents in other hair treating operations, for example, in permanent waving operations.

The cosmetic compositions in accordance with the invention are, principally, cosmetic compositions for the hair characterized by the fact that they contain at least one polymer of formula (I).

These cosmetic compositions for the hair can be provided in the form of aqueous, alcoholic or hydroalcoholic solutions, the alcohol being either ethanol or isopropanol, or in the form of a cream, a gel, an emulsion or even in the form of a spray. In this latter case, the compositions are packaged in an aerosol container, under pressure, together with a propellant such as nitrogen, nitrous oxide, carbon dioxide and fluorochlorinated hydrocarbons such as those known under the name of "Freon" or even mixtures of such propellants.

The adjuvants generally present in the cosmetic compositions for the hair, in accordance with the invention, are for example perfumes, dyes, preservatives, sequesterants, thickening agents, emulsifiers and the like, or even resins used in cosmetic compositions for the hair.

The cosmetic compositions for the hair, in accordance with the present invention, include principally:

(a) treating compositions characterized in that they contain as the active component at least one polymer of formula I in an aqueous or hydroalcoholic solution.

The amount of the polymer of formula (I) present therein can vary between 0.01 and 15 weight percent and preferably between 0.1 and 8 weight percent.

The pH of these compositions is close to neutral and it can vary, for example, from 6 to 8.

If necessary, the pH can be adjusted to the value desired by adding either an acid such as citric acid or a base, principally an alkanolamine such as monoethanolamine or triethanolamine.

To treat the hair with such a composition or lotion, the said lotion is applied to wet hair, and is permitted to remain in contact therewith for 3–15 minutes. Thereafter the hair is rinsed. Subsequently, if desired, the hair can be set;

(b) shampoo compositions characterized by the fact that they contain at least one polymer of formula (I) and a cationic, nonionic or anionic detergent.

The cationic detergents are principally long chain quaternary ammoniums, esters of fatty acids and amino alcohols or of polyether amines.

The nonionic detergents are principally esters of polyols and sugars, the condensation products of ethylene oxide on fatty bodies, on long chain alkyl phenols, on long chain mercaptans or on long chain amides and the polyethers of polyhydroxylated fatty alcohols.

The anionic detergents are principally alkaline salts, ammonium salts or the amines or amino alcohol salts of fatty acids such as oleic acid, ricin oleic acid, and the acids of copra oil or hydrogenated copra oil; the alkaline salts, ammonium salts or amino alcohol salts of the sulfates of fatty alcohols, principally $C_{12}$–$C_{14}$ and $C_{16}$ fatty alcohols; the alkaline salts, mangesium salts, ammonium salts or amino alcohol salts of the sulfates of oxyethylenated fatty alcohols; the condensation products of fatty acids with isethionates, with taurine, with methyl taurine, with sarcosine and the like; the alkyl benzene sulfonates, principally with the alkyl being $C_{12}$; the alkylaryl polyether sulfates; the mono-glyceride sulfates and the like.

All these detergents, as well as numerous others not listed above, are well known and are described in the literature.

These compositions in the form of shampoos can also contain various adjuvants such as for example, perfumes, dyes, preservatives, thickening agents, foam stabilizers, softening agents or even one or more cosmetic resins.

In these shampoo compositions, the detergent concentration is generally between 5 and 50 weight percent and the concentration of the copolymer of formula (I) is between 0.01 and 15 weight percent, preferably between 0.1 and 5 weight percent;

(c) hair setting lotions, principally for sensitized hair, characterized by the fact that they contain at least one polymer of formula (I) in an aqueous, alcoholic or hydroalcoholic solution.

The concentration of the copolymer of formula (I) in these hair setting lotions varies generally between 0.1 and 5 weight percent and preferably between 0.2 and 3 weight percent.

The pH of these hair setting lotions generally varies between 3 and 9, and preferably between 4.5 and 7.5;

(d) hair dye compositions characterized by the fact that they contain at least one polymer of formula (I), a hair dye and a vehicle or carrier. The carrier constitutes, preferably, a cream.

The concentration of the polymers of formula (I) in these hair dye compositions can vary between 0.5 and 15 weight percent and preferably between 0.5 and 10 weight percent.

In the case of an oxidation type hair dye composition, the same can be packaged in two parts, the first part containing the said polymer, dye and carrier; the second part containing hydrogen peroxide. The two parts are mixed at the time of use;

(e) hair lacquer compositions characterized by the fact that they contain an alcoholic or hydroalcoholic solution of at least one copolymer of formula (I), optionally combined with another resin, this solution being packaged under pressure in an aerosol container together with a liquified propellant.

For example, an excellent aerosol hair lacquer in accordance with the present invention can be obtained by admixing at least one copolymer of formula (I) with an anhydrous aliphatic alcohol, such as ethanol or isopropanol and with a propellant or a mixture of propellants such as those defined previously.

In these hair lacquer compositions, the concentration of the copolymers of formula (I) is generally between 0.5 and 3 weight percent.

However, as for the preceding compositions, it is possible to add to these lacquers various components such as dyes, plasticizers or any other conventional adjuvant;

(f) pre-treating compositions provided principally in the form of aqueous or hydroalcoholic solutions, optionally in aerosol containers, or in the form of creams or gels, these pre-treating compositions being destined to be applied to the hair before a shampooing, principally before an anionic or nonionic shampooing, before an oxidation dyeing followed by an anionic and/or nonionic shampooing, or before a permanent wave treatment.

In these pre-treating compositions, the copolymer of formula (I) constitutes the active component and its concentration varies generally between 0.1 and 15 weight percent and preferably between 0.2 and 8 weight percent.

The pH of these compositions is close to neutral and varies generally between 3 and 9, principally between 6 and 8.

These pre-treating compositions can contain various adjuvants conventionally employed in cosmetic compositions for the hair such as, for example, plasticizing agents, perfumes, dyes and the like.

In accordance with another embodiment of this invention, the copolymers of formula (I) can also be used in cosmetic compositions for the hair in combination with other polymers having an anionic or cationic character.

In accordance with such an embodiment, the polymer having an anionic or cationic character is present in the composition in an amount between 0.01 and 10 weight percent and preferably between 0.02 and 5 weight percent.

As has been indicated above, the cosmetic composition according to this invention can also be employed for the care or treatment of the skin.

In effect, these compositions facilitate the hydration of the skin and avoid its drying out. These compositions also impart to the skin excellent softness to the touch.

The cosmetic compositions for the skin are provided preferably in the form of creams, gels, emulsions or aqueous, alcoholic or hydroalcoholic solutions.

The concentration of the polymer of formula (I) in these compositions for the skin can vary between 0.1 and 15 weight percent and preferably between 0.2 and 6 weight percent.

The adjuvants generally present in these cosmetic compositions are, for example, perfumes, dyes, preservatives, thickening agents, suquesterants, emulsifiers, solar filters and the like.

These compositions for the skin constitute principally treating creams or lotions for the hands or face or indeed, anti-solar creams, dyeing creams, make-up remover milks, foamable bath liquids or even deodorant compositions.

These compositions are prepared according to known methods.

For example, to obtain a cream, an aqueous phase containing in solution the copolymer of formula (I) and optionally other components or adjuvants is emulsified with an oily phase.

The oily phase can be constituted by various compounds such as, for example, paraffin oil, petrolatum oil, sweet almond oil, avocado oil, olive oil, esters of fatty acids such as glyceryl monostearate, ethyl or isopropyl palmitates, alkyl myristates such as propyl, butyl or cetyl myristates. Fatty alcohols such as cetyl alcohol or waxes such as beeswax can also be added.

The copolymers of formula (I) can be present in these cosmetic compositions for the skin as an additive or as the principal active component.

The following non-limiting examples are provided to illustrate the invention. Unless otherwise stated, all parts and percentages are by weight.

EXAMPLES OF PREPARING THE COPOLYMERS OF FORMULA (I)

EXAMPLE 1

In a 1 liter round bottom flask, fitted with a mechanical agitator and a nitrogen lead-in tube, there are introduced 30 g (0.145 mole) of dimethyl diallylammonium bromide, 100 g of water and 1.2 g of t-butyl hydroperoxide in solution in 70 g (0.524 mole) of N-vinylpyrrolidone-2. The reaction mixture is heated to 70° C. and maintained at this temperature for 24 hours, with agitation. The solution is then left to cool and is slowly poured into 3 liters of acetone. The desired polymer precipitates and is filtered and dried at 40° C. under reduced pressure. Yield: 70%.

EXAMPLE 2

Utilizing the procedures of Example 1, there are copolymerized 25 g (0.225 mole) of N-vinylpyrrolidone-2, 38 g (0.242 mole) of N,N-dimethylamino-2-ethyl methacrylate and 37 g (0.179 mole) of dimethyl diallyl ammonium bromide, in the presence of 1 g of t-butyl hydroperoxide.

After precipitation and drying, the polymer is obtained with a yield of 56%.

In following Tables I to III are tabulated Examples 3 to 52, showing the preparation of various copolymers of formula I.

These copolymers have been prepared in accordance with the procedures of Example 1 by using the solvents and precipitation agents or other means of purification indicated in the Tables.

For all the Examples there has been used as the catalyst, t-butyl hydroperoxide except for Example 24 wherein azo-bis-isobutyronitrile has been used.

The compositions are expressed in molar fractions.

The symbols used in these Tables have the following meanings: A=water; a*=emulsion in water; a**=cold water; b=ethyl alcohol; c=methyl alcohol; d=acetone; e=petroleum ether; f=acetonitrile and g=dialysis.

TABLE I

| Examples | 3 | 4 | 5 | 6 | 7 | 8 | 9 | 10 | 11 | 12 | 13 | 14 | 15 | 16 | 17 | 18 | 19 | 20 | 21 |
|---|---|---|---|---|---|---|---|---|---|---|---|---|---|---|---|---|---|---|---|
| Dimethyl diallyl ammonium bromide | 0.45 | 0.5 | 0.2 | 0.4 | 0.5 | 0.2 | 0.65 | 0.45 | 0.45 | 0.3 | 0.8 | 0.5 | 0.48 | 0.75 | 0.3 | 0.5 | 0.65 | 0.3 | 0.4 |
| N—vinylpyrrolidone-2 | 0.1 | 0.05 | 0.2 | 0.2 | 0.3 | 0.7 | 0.25 | 0.45 | 0.45 | 0.6 | 0.05 | 0.35 | 0.40 | 0.10 | 0.6 | 0.4 | 0.3 | 0.2 | 0.4 |
| N,N—dimethylamino-2 ethyl methacrylate | 0.45 | | 0.6 | | | | | | | | | | | | | | | | |
| [(methacryloyloxy-2)ethyl-1] trimethylammonium methyl sulfate | | 0.45 | | 0.4 | 0.2 | 0.1 | | | | 0.1 | | | | | | | | | |
| Lauryl methacrylate | | | | | | | 0.1 | | | | | | | | | | | | |
| Isopropyl methacrylate | | | | | | | | | | | | | | | 0.1 | | 0.1 | | |
| Butyl methacrylate | | | | | | | | | 0.1 | | | | | | | | | | |
| Vinyl acetate | | | | | | | | | | | 0.15 | | | | | | | | |
| Vinyl laurate | | | | | | | | | | | | 0.15 | | | | | | | |
| Vinyl stearate | | | | | | | | | | | | | 0.12 | | | | | | |
| Vinyl butyrate | | | | | | | | | | | | | | 0.15 | | | | | |
| Cetyl vinyl ether | | | | | | | | | | | | | | | | 0.1 | | | |
| Isopropyl vinyl ether | | | | | | | | | | | | | | | | | 0.05 | | |
| Acrylamide | | | | | | | | | | | | | | | | | | 0.5 | 0.2 |
| SOLVENT | a | a | a | a | a | a | b | b | b | a | b | b | b | b | b | b | c | a | a |
| PRECIPITANT | d | d | d | d | d | d | d | c | c | d | f | d | d | f | d | d | f | d | d |

TABLE I-continued

| Examples | 3 | 4 | 5 | 6 | 7 | 8 | 9 | 10 | 11 | 12 | 13 | 14 | 15 | 16 | 17 | 18 | 19 | 20 | 21 |
|---|---|---|---|---|---|---|---|---|---|---|---|---|---|---|---|---|---|---|---|
| YIELD % | 40 | 50 | 60 | 65 | 60 | 45 | 35 | 30 | 25 | 30 | 34 | 23 | 28 | 32 | 40 | 30 | 20 | 40 | 34 |

TABLE II

| Examples | 22 | 23 | 24 | 25 | 26 | 27 | 28 | 29 | 30 | 31 | 32 | 33 | 34 | 35 | 36 | 37 | 38 |
|---|---|---|---|---|---|---|---|---|---|---|---|---|---|---|---|---|---|
| Dimethyl diallyl ammonium bromide | 0.2 | 0.4 | 0.3 | 0.3 | 0.7 | 0.45 | | | | | | | | 0.40 | | | |
| Methyl butyl diallyl ammonium bromide | | | | | | | 0.25 | | | | | 0.35 | | | | | |
| Methyl octyl diallyl ammonium bromide | | | | | | | | 0.20 | | | | 0.20 | | | | | |
| Methyl decyl diallyl ammonium bromide | | | | | | | | | 0.20 | | | | 0.35 | | 0.20 | 0.20 | |
| Methyl dodecyl diallyl ammonium bromide | | | | | | | | | | 0.20 | | | | | | | 0.20 |
| N—vinylpyrrolidone-2 | 0.4 | 0.3 | 0.3 | 0.4 | 0.1 | 0.50 | 0.50 | 0.50 | 0.50 | 0.70 | 0.50 | 0.70 | 0.30 | 0.40 | 0.20 | 0.55 | 0.60 |
| N—t-butylacrylamide | 0.2 | | | | | | | | | | 0.10 | 0.05 | 0.05 | 0.10 | 0.05 | | |
| N,N—dimethylamino-2 ethyl methacrylate | 0.2 | | | | | 0.25 | 0.30 | 0.30 | 0.10 | | 0.05 | 0.30 | | | | | |
| Vinyl acetate | | | | | | | | | | | 0.05 | | | | | 0.25 | 0.20 |
| Methacrylamide | | 0.1 | | | | | | | | | | | | 0.10 | | | |
| N—hydroxymethyl acrylamide | | | 0.4 | 0.3 | | | | | | | | | | | | | |
| Methyl acrylate | | | | | | 0.05 | | | | | | | | | | | |
| [(methyacryloyloxy-2) ethyl-1] trimethyl-ammonium methyl sulfate | | 0.2 | | | | | | | | | | | | | 0.55 | | |
| N—[(dimethyl-1,1-hydroxy-2)ethyl-1] acrylamide | | | | | 0.2 | | | | | | | | | | | | |
| SOLVENT | b | a | a | a | a | a | b | b | b | b | b | b | b | b | b | b | a* |
| PRECIPITANT or other purification | d | d | d | d | d | d | g | g | g | g | d | d | d | d | f | g | a** |
| YIELD % | 29 | 20 | 25 | 20 | 18 | 18 | 20 | 22 | 19 | 25 | 28 | 20 | 25 | 40 | 30 | 25 | 27 |

TABLE III

| Examples | 39 | 40 | 41 | 42 | 43 | 44 | 45 | 46 | 47 | 48 | 49 | 50 | 51 | 52 |
|---|---|---|---|---|---|---|---|---|---|---|---|---|---|---|
| Methyl butyl diallyl ammonium bromide | | 0.40 | | | | | | | | | | | | |
| Methyl octyl diallyl ammonium bromide | | | 0.20 | | | | | | | | | | | |
| Methyl dodecyl diallyl ammonium bromide | 0.25 | | | 0.20 | | | | | | | | | | |
| Dimethyl diallyl ammonium bromide | | | | | | | | | | | | | | 0.13 |
| Diallyl methyl ammonium hydrochloride | | | | | 0.80 | 0.90 | 0.80 | | | | | 0.3 | 0.7 | |
| Diallyl butyl ammonium hydrochloride | | | | | | | | 0.20 | | | | | | |
| Diallyl octyl ammonium hydrochloride | | | | | | | | | 0.20 | | | | | |
| Diallyl decyl ammonium hydrochloride | | | | | | | | | | | 0.30 | | | |
| Diallyl dodecyl ammonium hydrochloride | | | | | | | | | | 0.20 | | | | |
| N—vinylpyrrolidone-2 | 0.30 | 0.45 | 0.15 | 0.15 | 0.20 | 0.05 | 0.10 | 0.80 | 0.80 | 0.70 | 0.80 | 0.7 | 0.3 | 0.65 |
| Lauryl methacrylate | | | 0.05 | | | | | | | | | | | |
| Stearyl methacrylate | | 0.05 | | | | | | | | | | | | |
| Acrylamide | 0.1 | | | 0.20 | | 0.05 | | | | | | | | |
| N—t-butyl-acrylamide | | | | | | | 0.10 | | | | | | | |
| N,N—dimethylamino-2-ethyl methacrylate | 0.30 | | | | | | | | | | | | | 0.22 |
| [(methacryloyloxy-2) ethyl]-1 trimethyl ammonium methyl sulfate | | 0.10 | 0.60 | 0.45 | | | | | | | | | | |
| SOLVENT | a | b | b | a | a | a | b | a | a | a | a | a | a | b |
| PRECIPITANT or other purification | g | d | f | f | d | d | d | g | g | g | g | g | g | e |

TABLE III-continued

| Examples | 39 | 40 | 41 | 42 | 43 | 44 | 45 | 46 | 47 | 48 | 49 | 50 | 51 | 52 |
|---|---|---|---|---|---|---|---|---|---|---|---|---|---|---|
| YIELD % | 25 | 34 | 40 | 20 | 30 | 25 | 20 | 25 | 25 | 30 | 30 | 32 | 28 | 46 |

EXAMPLE 53

Preparation of the copolymer of Example 44 in non-salified form.

10 g of the copolymer prepared in accordance with Example 44 are dissolved in 100 g of water with agitation at ambient temperature. To this solution there is added 0.1 M sodium hydroxide in an amount sufficient so that the pH of the solution is between 12 and 13. Agitation is maintained for 1 hour. The solution is then filtered. The polymer is recovered in the form of a white precipitate. Yield: 40%.

EXAMPLES 54 AND 55

In accordance with the procedures described in Example 53, the polymers of Examples 43 and 45 have also been obtained in non-salified form with a final yield between 35 and 60 percent.

EXAMPLES 56 TO 62

The polymers of Examples 46 to 52 have been treated under the same conditions as those described in Example 53 above. However, the solutions obtained are not filtered but evaporated to dryness under reduced pressure at 50° C. The residues are then taken up in acetone and filtered. The polymers are isolated after evaporation of the acetone. Yield: about 30 to 35%.

Examples of Cosmetic Compositions

EXAMPLE A

A treating composition destined to be applied after a shampooing is prepared by admixing the following components:
Petrolatum oil—15 g
Cetyl stearyl alcohol—2.5 g
Cetyl stearyl alcohol polyoxyethylenated with 10 moles of ethylene oxide—2.5 g
Copolymer of Example 1—1.2 g
Water, sufficient for—100 g
pH=4.4

This composition is applied to wet hair for a few minutes. The hair is then rinsed. One obtains excellent combing of the hair which is shiny and easy to style.

In this Example, the polymer obtained in accordance with Example 1 can be replaced by the same amount of one of the polymers prepared in accordance with Examples 4, 5-8 and 46-52.

EXAMPLE B

A hair setting lotion is prepared by admixing the following components:
Copolymer of Example 2—1.5 g
Ethyl alcohol—50 g
Perfume—0.1 g
Dye—0.4 g
Water, sufficient for—100 g
pH=5

After application of this lotion, the hair combs easily, is shiny, lively and non-electric.

In this Example, the polymer obtained according to Example 2 can advantageously be replaced by the same amount of one of the polymers prepared in accordance with Examples 9-15 and 34-42.

EXAMPLE C

A hair setting lotion is prepared by admixing the following components:
Copolymer of Example 3—0.5 g
Quaternary polyvinylpyrrolidone polymer, M.W.=100,000, sold under the name "GAFQUAT 734"—0.5 g
Quaternized cellulose, sold under the name "JR 400"—0.3 g
Ethyl alcohol—15 g
Perfume—0.3 g
Dye—0.2 g
Water, sufficient for—100 g
pH, adjusted to 8.

This hair setting lotion applied to bleached hair provides excellent combing of wet hair. After drying the hair, one obtains excellent setting, the hair being soft to the touch, shiny and easy to style.

in this Example, the polymer obtained in accordance with Example 3 can be replaced by the same amount of one of the polymers prepared in accordance with Examples 16-25, 44 and 45.

EXAMPLE D

A hair brushing lotion is prepared by admixing the following components:
Copolymer of Example 4—0.6 g
Trimethylcetyl ammonium bromide—0.2 g
Perfume—0.2 g
Dye—0.4 g
Water, sufficient for—100 g
pH=6.5

This lotion is applied to natural hair dried following a brushing technique. The passage of the brush through the hair is facilitated and the dry hair is soft, shiny and non-electric.

In this Example, the polymer obtained in accordance with Example 4 can be replaced by the same amount of one of the polymers obtained in accordance with Examples 19-21 and 23-26.

EXAMPLE E

A shampoo composition is prepared by admixing the following components:
Sodium lauryl ether sulfate (2.2 moles of ethylene oxide)—14 g
Lauric diethanolamide—3 g
Copolymer of Example 2—1 g
Perfume—0.15 g
Dye—0.2 g
Water, sufficient for—100 g
pH, adjusted to 7.5 by the addition of lactic acid

EXAMPLE F

A pre-shampoo composition is prepared by admixing the following components:
Copolymer of Example 6—1 g
Trimethylcetyl ammonium bromide—1 g
Propylene glycol, sufficient for—100 g pH=7.2

This product is applied before shampooing the hair. After permitting the same to remain in contact with the hair for a few minutes, the hair is rinsed. The combing of the wet hair is facilitated. After shampooing the hair and setting the hair, it is lively and easy to style.

In this Example, the polymer obtained in accordance with Example 6 can be replaced by the same amount of one of the polymers obtained in accordance with Examples 27–34 and 53–62.

EXAMPLE G

A capillary treating cream is prepared by admixing the following components:

Cetyl stearyl alcohol oxyethylenated with 2 moles of ethylene oxide, sold under the name "BRIJ 72"—18 g
Polymer of Example 1—1 g
Water, sufficient for—100 g 60 to 80 g of this cream are applied to clean damp and dried hair, in a manner to impregnate it and to cover all the hair.

After permitting the cream to remain in contact with the hair for 15–20 minutes, the hair is rinsed. The wet hair is soft and easy to comb. After setting the hair, it is easily combed and has a silky touch. Moreover, the hair is shiny and lively, it has body and fullness.

In this Example, the polymer obtained in accordance with Example 1 can be replaced by the same amount of one of the polymers prepared in accordance with Examples 29–42.

EXAMPLE H

A hair dye composition in the form of a cream is prepared by admixing the following components:

Cetyl alcohol—18 g
Ammonium lauryl sulfate (30% active material)—12 g
Stearyl alcohol oxyethylenated with 15 moles of ethylene oxide—3 g
Lauryl alcohol—5 g
Copolymer of Example 2—3 g
Ammonia, 22° Be—12 ml
Meta Diamino anisole sulfate—0.048 g
Resorcinol—0.420 g
Meta amino phenol base—0.150 g
Nitro paraphenylene diamine—0.085 g
Para toluylene diamine—0.004 g
Ethylene diamine tetra—acetic acid—1 g
Sodium bisulfite, d=1.3—1.2 g
Water, sufficient for—100 g 30 g of this formulation are mixed with 45 g of hydrogen peroxide (20 volumes). A cream having a smooth consistency is obtained which is pleasant to apply and which adheres well to the hair.

This cream is applied to the hair with a brush and is permitted to remain in contact therewith for 30 minutes. The hair is then rinsed.

The hair combs easily and is silky to the touch. On 100% white hair a blonde coloration is achieved.

In this Example, the polymer obtained in accordance with Example 2 can be replaced by the same amount of one of the polymers prepared in accordance with Examples 35, 42 and 53–62.

EXAMPLE I

A hair structuring lotion is prepared by admixing at the moment of use, the following components:

Dimethylol ethylene thiourea—1.6 g
Copolymer of Example 1—1.2 g
HCl, sufficient for a pH=2,7
Water, sufficient for—100 ml This lotion is applied to washed and dried hair before setting it. After setting the hair, it is shiny and lively; it has body and fullness; and the hair is silky and easy to comb.

In this Example, the copolymer obtained in accordance with Example 1 can advantageously be replaced by 0.5 g of the copolymer obtained according to Example 2. Equally excellent results are obtained.

EXAMPLE K

An aerosol hair lacquer is obtained by admixing the following components:

Copolymer of Example 28—6.5 g
Perfume—0.2 g
Ethanol, sufficient for—100 g 25 g of this composition are packaged in an aerosol container, under pressure, together with 45 g of trichlorofluoromethane and 30 g of dichlorodifluoromethane.

There is thus obtained after spraying the product on the hair a film having excellent qualities. The hair thus treated is shiny and soft to the touch.

In this Example, the polymer obtained in accordance with Example 28 can be replaced by the same amount of one of the polymers obtained in accordance with Examples 22, 29, 30, 53–55 and 60,

EXAMPLE L

An aerosol hair lacquer composition is prepared by admixing the following components:

Polymer of Example 30—5 g
Perfume—0.07 g
Ethanol, sufficient for—100 g 93 g of this solution are packaged, under pressure, in an aerosol container together with a sufficient amount of $CO_2$ to provide an internal pressure of 8 bars.

As in the preceding Example, there is obtained on spraying the above composition, excellent lacquering of the hair.

The polymer obtained in accordance with Example 30 can advantageously be replaced by the same amount of one of the polymers prepared in accordance with Examples 22, 29 and 53.

EXAMPLE M

A shampoo composition is prepared by admixing the following components:

Polymer of Example 52—0.6 g
Acrylamide polymer, sold under the name "VERSICOL E-5" and neutralized with NaOH—0.3 g Compound of the formula:

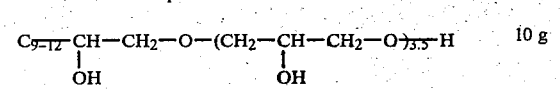

$C_{9-12}$—CH—CH$_2$—O—(CH$_2$—CH—CH$_2$—O)$_{3.5}$—H  10 g
      |                       |
      OH                      OH

HCl, sufficient for a pH=8.8
Water—100 g

EXAMPLE N

A shampoo composition is prepared by admixing the following components:

Polymer of Example 1—0.6 g

Butyl monoester of methyl vinyl ether/maleic anhydride copolymer sold under the name "GANTREZ ES-425", neutralized with NaOH—0.4 g Compound of the formula:

$$C_{9-12}-CH-CH_2-O-(CH_2-CH-CH_2-O)_{3.5}-H \quad 15\,g$$
$$\quad\quad\;\; |\quad\quad\quad\quad\quad\quad\quad\; |$$
$$\quad\quad\; OH\quad\quad\quad\quad\quad\quad\; OH$$

HCl, sufficient for pH=6
Water, sufficient for—100 g

EXAMPLE O

A shampoo composition is prepared by admixing the following components:
Polymer of Example 1—0.7 g
Vinyl acetate/crotonic acid/vinyl neodecanoate polymer, sold under the name "Resine 28 29 30" neutralized with NaOH—0.35 g Compound of the formula:

$$C_{12-14}-(OCH_2-CH_2)_{10}-O-CH_2-COOH \quad 10\,g$$

NaOH, sufficient for pH=9.2
Water, sufficient for—100 g

What is claimed is:

1. A cosmetic composition for the care of the hair and skin to prevent dryness and roughness comprising in a cosmetic vehicle selected from the group consisting of water, alcohol and a hydroalcoholic solution 0.01 to 15 percent by weight of a copolymer having one or both of tertiary amine and quaternary ammonium functions, said copolymer having the formula (I)

Ia

Ib

Ic    Id wherein:

$R_1$, $R_4$ and $R_5$ each independently represent alkyl having 1–12 carbon atoms, $R_2$ and $R_3$ each independently represent hydrogen or methyl, $R'$ and $R''$ each independently represent hydrogen or lower alkyl having 1–4 carbon atoms, l is 0 or 1, if l=0, t=1 and if l=1, t=0, n is 0, 1 or 2, is 0 or 1, A represents chloride or bromide, HX is an acid selected from the group consisting of hydrochloric acid, hydrobromic acid, acetic acid and lactic acid, M represents a unit of an unsaturated monomer selected from the group consisting of
(i) a vinyl ester of the formula $$R_5-\overset{\overset{\displaystyle O}{\|}}{C}-O-CH=CH_2$$

wherein $R_5$ represents alkyl having 1–17 carbon atoms,
(ii) a vinyl ether of the formula $R_6-O-CH=CH_2$ wherein $R_6$ represents alkyl having 1–16 carbon atoms,
(iii) an acrylic or methacrylic ester of the formula $$CH_2=\underset{\underset{\displaystyle R'''}{|}}{C}-\overset{\overset{\displaystyle O}{\|}}{C}-O-R_7$$

wherein $R'''$ represents a member selected from the group consisting of hydrogen and methyl and $R_7$ represents a member selected from the group consisting of alkyl having 1–18 carbon atoms, alkyl having 1–3 carbon atoms and substituted by at least one alkoxy having 1–4 carbon atoms and $$-CH_2-CH_2-N{\overset{\displaystyle r'}{\underset{\displaystyle r''}{<}}}$$

wherein $r'$ and $r''$ each independently represent alkyl having 1–4 carbon atoms, and
(iv) an acrylamide or methacrylamide of the formula $$CH_2=\underset{\underset{\displaystyle R'_1}{|}}{C}-\overset{\overset{\displaystyle O}{\|}}{C}-N{\overset{\displaystyle R_8}{\underset{\displaystyle R_9}{<}}}$$

wherein $R_8$ and $R_9$ each independently represent a member selected from the group consisting of hydrogen, alkyl having 1–4 carbon atoms and $-(CH_2)_m-OH$ wherein m is equal to 1, 2 or 3 and $R'_1$ represents a member selected from the group consisting of hydrogen and methyl;

$x+x'$ corresponds to 95–5 mole percent wherein one of x and x' can be 0;

y corresponds to 5–95 mole percent; and z corresponds to 0–60 mole percent, with $(x+x')+y+z$ being equal to 100 mole percent; and from 0.01 to 10 weight percent of another polymer having an anionic or cationic character and cosmetic adjuvants.

2. The cosmetic composition of claim 1 wherein said another polymer is present in an amount between 0.02 and 5 weight percent thereof.

3. A cosmetic composition for the care of the hair and skin comprising in a cosmetic vehicle selected from the group consisting of water, alcohol and a hydroalcoholic solution 0.01 to 15 percent by weight of a copolymer having one or both of tertiary amine and quaternary ammonium functions, said copolymer having the formula:

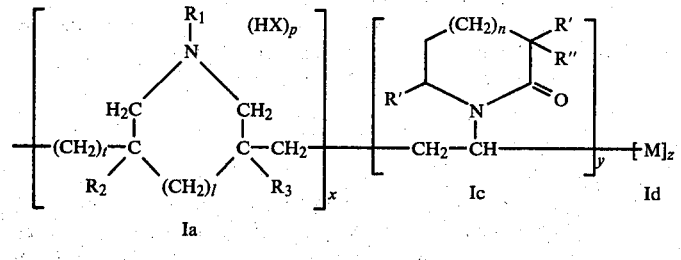

wherein
$R_1$ represents alkyl having 1-12 carbon atoms,
$R_2$ and $R_3$ each independently represent hydrogen or methyl,
$R'$ and $R''$ each independently represent hydrogen or lower alkyl having 1-4 carbon atoms
l is 0 or 1, if l=0, t=1 and if l=1, t=0,
n is 0, 1 or 2,
p is 0 or 1,
HX is an acid selected from the group consisting of hydrochloric acid, hydrobromic acid, acetic acid and lactic acid,
M represents a unit of an unsaturated monomer selected from the group consisting of
(i) a vinyl ester of the formula

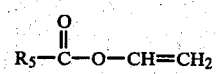

wherein $R_5$ represents alkyl having 1-17 carbon atoms,
(ii) a vinyl ether of the formula $R_6$—O—CH=CH$_2$ wherein $R_6$ represents alkyl having 1-16 carbon atoms,
(iii) an acrylic or methacrylic ester of the formula

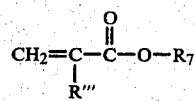

wherein $R'''$ represents a member selected from the group consisting of hydrogen and methyl and $R_7$ represents a member selected from the group consisting of alkyl having 1-18 carbon atoms, alkyl having 1-3 carbon atoms and substituted by at least one alkoxy having 1-4 carbon atoms and

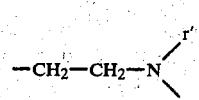

wherein $r'$ and $r''$ each independently represent alkyl having 1-4 carbon atoms, and
(iv) an acrylamide or methacrylamide of the formula

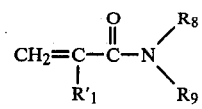

wherein $R_8$ and $R_9$ each independently represent a member selected from the group consisting of hydrogen, alkyl having 1-4 carbon atoms and —(CH$_2$)$_m$—OH wherein m is equal to 1, 2 or 3 and $R'_1$ represents a member selected from the group consisting of hydrogen and methyl;
x corresponds to 95-5 mole percent,
y corresponds to 5-95 mole percent, and
z corresponds to 0-60 mole percent.

4. A hair shampoo composition comprising in a cosmetic vehicle selected from the group consisting of water and a hydroalcoholic solution 0.01 to 15 percent by weight of a copolymer having one or both of tertiary amine and quaternary ammonium functions, said copolymer having the formula

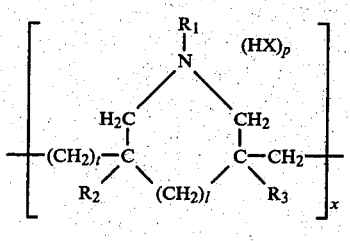

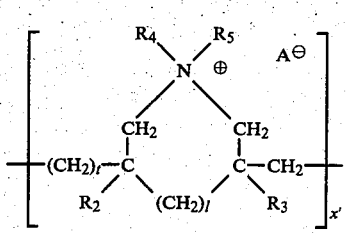

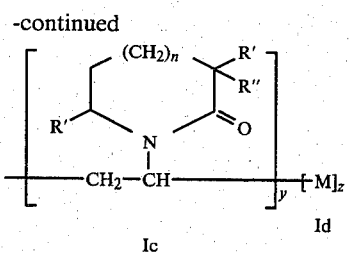

wherein:
R₁ R₄ and R₅ each independently represent alkyl having 1–12 carbon atoms,
R₂ and R₃ each independently represent hydrogen or methyl,
R' and R'' each independently represent hydrogen or lower alkyl having 1–4 carbon atoms,
l is 0 or 1, if l=0, t=1 and if l=1, t=0,
n is 0, 1 or 2,
p is 0 or 1,
A represents chloride or bromide,
HX is an acid selected from the group consisting of hydrochloric acid, hydrobromic acid, acetic and acid and lactic acid,
M represents a unit of an unsaturated monomer selected from the group consisting of
(i) a vinyl ester of the formula

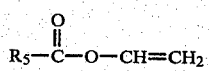

wherein R₅ represents alkyl having 1–17 carbon atoms,
(ii) a vinyl ether of the formula R₆—O—CH=CH₂ wherein R₆ represents alkyl having 1–16 carbon atoms,
(iii) an acrylic or methacrylic ester of the formula

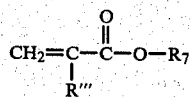

wherein R''' represents a member selected from the group consisting of hydrogen and methyl and R₇ represents a member selected from the group consisting of alkyl having 1–18 carbon atoms, alkyl having 1–3 carbon atoms and substituted by at least one alkoxy having 1–4 carbon atoms and

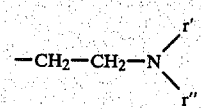

wherein r' and r'' each independently represent alkyl having 1–4 carbon atoms, and
(iv) an acrylamide or methacrylamide of the formula

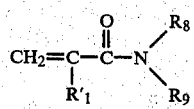

wherein R₈ and R₉ each independently represent a member selected from the group consisting of hydrogen, alkyl having 1–4 carbon atoms and —(CH₂)ₘ—OH wherein m is equal to 1, 2 or 3 and R'₁ represents a member selected from the group consisting of hydrogen and methyl;
x+x' corresponds to 95–5 mole percent wherein one of x and x' can be 0;
y corresponds to 5–95 mole percent; and
z corresponds to 0–60 mole percent, with (x+x')+y+z being equal to 100 mole percent; and between 5 and 50 weight percent of a cationic, nonionic or anionic detergent and cosmetic adjuvants.

5. An aerosol hair lacquer composition comprising in a cosmetic vehicle selected from the group consisting of alcohol and a hydroalcoholic solution 0.01 to 15 percent by weight of a copolymer having one or both of tertiary amine and quaternary ammonium functions, said copolymer having the formula:

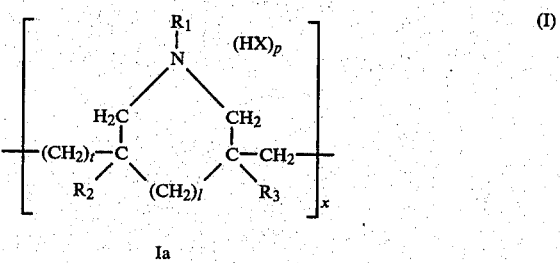

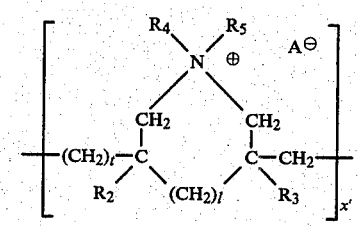

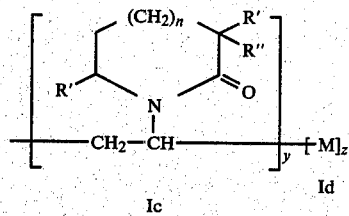

wherein:
R₁, R₄ and R₅ each independently represent alkyl having 1–12 carbon atoms,
R₂ and R₃ each independently represent hydrogen or methyl,
R' and R'' each independently represent hydrogen or lower alkyl having 1–4 carbon atoms,
l is 0 or 1, if l=0, t=1 and if l=1, t=0,
n is 0, 1 or 2,
p is 0 or 1,
A represents chloride or bromide,
HX is an acid selected from the group consisting of hydrochloric acid, hydrobromic acid, acetic acid and lactic acid,
M represents a unit of an unsaturated monomer selected from the group consisting of (i) a vinyl ester of the formula

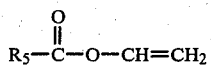

wherein $R_5$ represents alkyl having 1-17 carbon atoms, (ii) a vinyl ether of the formula $R_6$—O—CH=CH$_2$ wherein $R_6$ represents alkyl having 1-16 carbon atoms, (iii) an acrylic or methacrylic ester of the formula

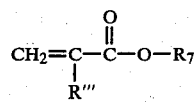

wherein $R'''$ represents a member selected from the group consisting of hydrogen and methyl and $R_7$ represents a member selected from the group consisting of alkyl having 1-18 carbon atoms, alkyl having 1-3 carbon atoms and substituted by at least one alkoxy having 1-4 carbon atoms and

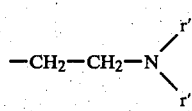

wherein $r'$ and $r''$ each independently represent alkyl having 1-4 carbon atoms, and (iv) an acrylamide or methacrylamide of the formula

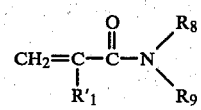

wherein $R_8$ and $R_9$ each independently represent a member selected from the group consisting of hydrogen, alkyl having 1-4 carbon atoms and —(CH$_2$)$_m$—OH wherein m is equal to 1, 2 or 3 and $R'_1$ represents a member selected from the group consisting of hydrogen and methyl;

$x+x'$ corresponds to 95-5 mole percent wherein one of x and x' can be 0;

y corresponds to 5-95 mole percent; and z corresponds to 0-60 mole percent, with $(x+x')+y+z$ being equal to 100 mole percent, and an effective amount of a liquefied propellant under pressure, said composition being packaged in an aerosol container.

6. A process for imparting to the skin and hair a natural and agreeable appearance and an agreeable touch or feel comprising applying thereto an effective amount of a cosmetic composition comprising in a cosmetic vehicle selected from the group consisting of water, alcohol and a hydroalcoholic solution 0.01 to 15 percent by weight of a copolymer having one or both of tertiary amine and quaternary ammonium functions, said copolymer having the formula:

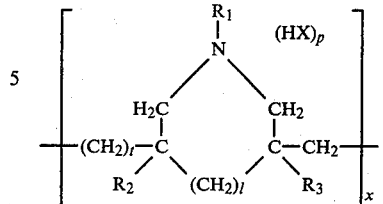

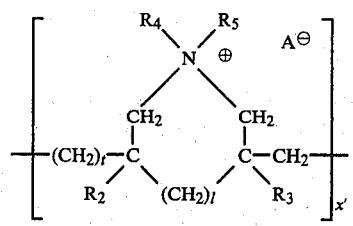

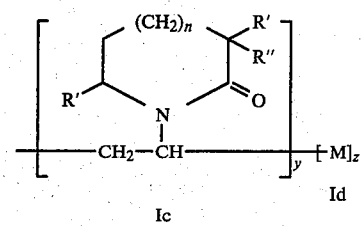

wherein:
$R_1$, $R_4$ and $R_5$ each independently represent alkyl having 1-12 carbon atoms, $R_2$ and $R_3$ each independently represent hydrogen or methyl, $R'$ and $R''$ each independently represent hydrogen or lower alkyl having 1-4 carbon atoms, l is 0 or 1, if l=0, t=1 and if l=1, t=0, n is 0, 1 or 2, p is 0 or 1, A represents chloride or bromide, HX is an acid selected from the group consisting of hydrochloric acid, hydrobromic acid, acetic acid and lactic acid, M represents a unit of an unsaturated monomer selected from the group consisting of (i) a vinyl ester of the formula

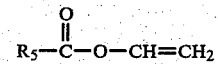

wherein $R_5$ represents alkyl having 1-17 carbon atoms, (ii) a vinyl ether of the formula $R_6$—O—CH=CH$_2$ wherein $R_6$ represents alkyl having 1-16 carbon atoms, (iii) an acrylic or methacrylic ester of the formula

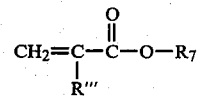

wherein $R'''$ represents a member selected from the group consisting of hydrogen and methyl and $R_7$ represents a member selected from the group consisting of alkyl having 1-18 carbon atoms, alkyl having 1-3 carbon atoms and substituted by at least one alkoxy having 1-4 carbon atoms and

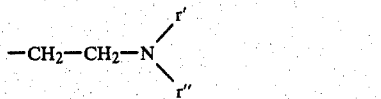

wherein r' and r" each independently represent alkyl having 1-4 carbon atoms, and (iv) an acrylamide or methacrylamide of the formula

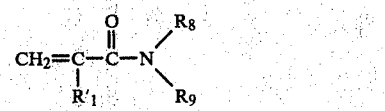

wherein $R_8$ and $R_9$ each independently represent a member selected from the group consisting of hydrogen, alkyl having 1-4 carbon atoms and $-(CH_2)_m-OH$ wherein m is equal to 1, 2 or 3 and $R'_1$ represents a member selected from the group consisting of hydrogen and methyl;

x+x' corresponds to 95-5 mole percent wherein one of x and x' can be 0;

y corresponds to 5-95 mole percent; and z corresponds to 0-60 mole percent, with (x+x')+y+z being equal to 100 mole percent.

7. A process for imparting to the skin and hair a natural and agreeable appearance and an agreeable touch or feel comprising applying thereto an effective amount of a cosmetic composition comprising in a cosmetic vehicle selected from the group consisting of water, alcohol and a hydroalcoholic solution 0.01 to 15 percent by weight of a copolymer having one or both of tertiary amine and quaternary ammonium functions, said copolymer having (a) x mole percent units of a cyclopolymerized salified diallyl alkylamine selected from the group consisting of diallyl methyl ammonium hydrochloride, diallyl butyl ammonium hydrochloride, diallyl octyl ammonium hydrochloride, diallyl decyl ammonium hydrochloride and diallyl dodecyl ammonium hydrochloride;

(b) x' mole percent units of a cyclopolymerized quaternary ammonium salt selected from the group consisting of dimethyl diallyl ammonium bromide, methyl butyl diallyl ammonium bromide, methyl octyl diallyl ammonium bromide, methyl decyl diallyl ammonium bromide and methyl dodecyl diallyl ammonium bromide, wherein x+x' corresponds to 95-5 mole percent wherein one of x and x' can be 0;

(c) y mole percent units of N-vinyl pyrrolidone-2 wherein y is 5-95 mole percent; and (d) z mole percent units of an unsaturated monomer selected from the group consisting of vinyl acetate, vinyl butyrate, vinyl laurate, vinyl stearate, isopropyl vinyl ether, cetyl vinyl ether, methyl acrylate, isopropyl methacrylate, butyl methacrylate, lauryl methacrylate, stearyl methacrylate, N,N-dimethylamino-2-ethyl methacrylate, tri methyl ammonium sulfate, acrylamide, methacrylamide, N-tert.butyl acrylamide, N-(1,1-dimethyl-2-hydroxy)1-ethylacrylamide and N-hydroxymethyl acrylamide, wherein z is 0-60 mole percent, with (x+x')+y+z being equal to 100 mole percent.

* * * * *